(12) United States Patent
Ohayon et al.

(10) Patent No.: US 9,949,716 B2
(45) Date of Patent: Apr. 24, 2018

(54) METHOD FOR GENERATING AN ELASTICITY IMAGE

(71) Applicant: UNIVERSITE JOSEPH FOURIER—GRENOBLE 1, St. Martin d'Hères (FR)

(72) Inventors: Jacques Ohayon, Tresserve (FR); Flavien Deleaval, Laissaud (FR); Guy Cloutier, Repentigny (CA)

(73) Assignees: Universite Joseph Fourier—Grenoble 1, St. Martin D'Heres (FR); Val-Chum, Limited Partnership, Montreal, Quebec (CA)

( * ) Notice: Subject to any disclaimer, the term of this patent is extended or adjusted under 35 U.S.C. 154(b) by 185 days.

(21) Appl. No.: 14/769,685

(22) PCT Filed: Feb. 17, 2014

(86) PCT No.: PCT/EP2014/053030
§ 371 (c)(1),
(2) Date: Aug. 21, 2015

(87) PCT Pub. No.: WO2014/128084
PCT Pub. Date: Aug. 28, 2014

(65) Prior Publication Data
US 2016/0007952 A1    Jan. 14, 2016

(30) Foreign Application Priority Data

Feb. 22, 2013    (FR) ...................................... 13 51549

(51) Int. Cl.
*A61B 8/08*    (2006.01)
*A61B 5/02*    (2006.01)
(Continued)

(52) U.S. Cl.
CPC ........ *A61B 8/0891* (2013.01); *A61B 5/02007* (2013.01); *A61B 8/485* (2013.01);
(Continued)

(58) Field of Classification Search
CPC . A61B 8/0891; A61B 8/5246; A61B 5/02007; A61B 8/485; A61B 5/021; G01S 7/52042
See application file for complete search history.

(56) References Cited

U.S. PATENT DOCUMENTS

| | | | | |
|---|---|---|---|---|
| 6,165,128 | A | * | 12/2000 | Cespedes ........... A61B 5/02007 600/463 |
| 7,318,804 | B2 | * | 1/2008 | Weitzel .................. A61B 8/485 600/438 |

(Continued)

FOREIGN PATENT DOCUMENTS

| | | |
|---|---|---|
| EP | 0908137 A1 | 4/1999 |
| EP | 1475040 A2 | 11/2004 |

OTHER PUBLICATIONS

Hansen et al. "Noninvasive vascular displacement estimation for relative elastic modulus reconstruction in transversal imaging planes". Sensors. (Mar. 11, 2013) 13(3): 3341-3357.*

(Continued)

*Primary Examiner* — Long V Le
*Assistant Examiner* — Angela M Hoffa
(74) *Attorney, Agent, or Firm* — Harness, Dickey & Pierce, PLC

(57) ABSTRACT

An image processing method enables an elasticity image of a body including a cavity to be produced on the basis of the material(s) forming the body, wherein the method includes the steps of:
  receiving a deformation image illustrating a field of movement of the points of the body on the basis of a pressure difference in the body,
(Continued)

estimating a shape function of the body from the deformation image, calculating an elasticity image of the body on the basis of the shape function, of the pressure difference and of the deformation image.

8 Claims, 2 Drawing Sheets

(51) Int. Cl.
*G01S 7/52* (2006.01)
*A61B 5/021* (2006.01)

(52) U.S. Cl.
CPC ........ *A61B 8/5246* (2013.01); *G01S 7/52042* (2013.01); *A61B 5/021* (2013.01)

(56) References Cited

U.S. PATENT DOCUMENTS

| | | | | |
|---|---|---|---|---|
| 8,249,324 | B2* | 8/2012 | Yokota | A61B 5/02007 382/128 |
| 8,660,326 | B2 | 2/2014 | Ohayon et al. | |
| 8,965,487 | B2* | 2/2015 | Bouma | A61B 5/0059 600/476 |
| 9,330,461 | B2* | 5/2016 | Zheng | A61B 6/5217 |
| 2005/0124892 | A1* | 6/2005 | Weitzel | A61B 8/485 600/449 |
| 2006/0058592 | A1* | 3/2006 | Bouma | A61B 5/0059 600/301 |
| 2007/0282202 | A1* | 12/2007 | Maurice | A61B 5/02007 600/438 |
| 2009/0198129 | A1* | 8/2009 | Varghese | A61B 8/0858 600/438 |
| 2010/0160778 | A1 | 6/2010 | Eskandari et al. | |
| 2010/0312092 | A1* | 12/2010 | Maurice | A61B 5/02007 600/411 |
| 2011/0282182 | A1* | 11/2011 | Ohayon | G06T 7/0012 600/407 |
| 2014/0147028 | A1* | 5/2014 | Zheng | A61B 6/5217 382/131 |
| 2015/0327835 | A1* | 11/2015 | Kim | A61B 8/48 600/438 |
| 2016/0196645 | A1* | 7/2016 | Ohayon | A61B 8/0891 382/131 |

OTHER PUBLICATIONS

Holzapfel et al. "Computational approaches for analyzing the mechanics of atherosclerotic plaques: A review". J of Biomechanics 47 (2014) 859-869.*

Deleaval, Flavien, et al., "The Intravascular Ultrasound Elasticity-Palpography Technique Revisited: A Reliable Tool for the in vivo Detection of Vulnerable Coronary Atherosclerotic Plaques," Ultrasound in Med. & Boil., vol. 39, No. 8, Mar. 1, 2013, pp. 1469-1481.

Céspedes, E. I., et al., "Intraluminal Ultrasonic Palpation: Assessment of Local and Cross-Sectional Tissue Stiffness," Ultrasound in Med. & Biol., vol. 26, No. 3, 2000, pp. 385-396.

Bouvier, Adeline, et al.; "A Direct Vulnerable Atherosclerotic Plaque Elasticity Reconstruction Method Based on an Original Material-Finite Element Formulation: Theoretical Framework," Physics in Medicine and Biology, vol. 58, No, 23, Dec. 7, 2013, pp. 8457-8476.

Doyley, M. M., et al.; "Evaluation of an Iterative Reconstruction Method for Quantitative Elastography," Phys. Med. Biol., 45, 2000, pp. 1521-1540.

Doyley, M. M.; "Model-Based Elastography: A Survey of Approaches to the Inverse Elasticit Problem," Phys. Med. Biol., 57, Jan. 6, 2012, pp. R35-R73.

Le Floc'h, Simon, et al.; "On the Potential of a New IVUS Elasticity Modulus Imaging Appraoch for Detecting Vulernable Atherosclerotic Coronary Plaques: in vitro Vessel Phantom Study," Phys. Med. Biol., Sep. 8, 2010, pp. 5701-5721.

Le Floc'h, Simon, et al.: "Vulnerable Atherosclerotic Plaque Elasticity Reconstruction Based on a Segmentation-Driven Optimization Procedure Using Strain Measurements: Theoretical Framework," IEEE Transactions on Medical Imagining, vol. 28, No. 7, Jul. 2009, pp. 1126-1137.

Moss, Nicolas, et al.; "A Finite Element Method for Crack Growth Without Remeshing," International Journal for Numerical Methods in Engineering, vol. 46, Sep. 10, 1999, pp. 131-150.

Oberai, Assad A., et al.; "Solution of Inverse Problems in Elasticity Imaging Using the Adjoint Method," Inverse Problems, 19, 2003, pp. 297-313.

Zhu, Yanning, et al.; "A Finite-Element Approach for Young's Modulus Reconstruction," IEEE Transactions on Medical Imaging, vol. 22, No. 7, Jul. 2003, pp. 890-901.

* cited by examiner

METHOD FOR GENERATING AN ELASTICITY IMAGE

CROSS-REFERENCE TO RELATED APPLICATIONS

This application is a National Phase Entry of International Application Serial No. PCT/EP2014/053030, filed on Feb. 17, 2014, which claims priority to French Application Serial No. 1351549, filed on Feb. 22, 2013, both of which are incorporated by reference herein.

TECHNICAL FIELD

The present invention relates to the general technical field of rigidity palpography. More precisely, the present invention relates to a method for generating a Young's modulus elasticity image of a composite medium surrounding a cavity. The present invention can have numerous applications. It can especially be applied to the estimation of a rupture risk of an atheromatous plaque.

BACKGROUND

Atheroma or atherosclerosis corresponds to a rearrangement of the intima of large- and average-sized arteries (aorta, coronary arteries, cerebral arteries, low limber arteries, etc.) by segmental accumulation of lipids, complex carbohydrates, blood and blood products, fatty tissues, calcareous deposits, and other minerals. This vascular pathology generally has a slow progression (over decades). It may stabilize and not represent a significant danger for the patient. But it may also degenerate into an instable form leading to a rupture of the plaque, and, within a few days, and cause lethal or morbid cardiovascular or cerebral accidents (CVA).

Indeed, the rupture of a plaque brings its contents into contact with the blood conveyed by the artery, which can result in the formation of a thrombus. The latter disturbs the bloodstream in the affected artery. It can also detach and be transported by the bloodstream, and, in the most severe cases, totally obstructs the lumen of the artery, stop the blood supply of the post-lesion region and lead to the ischemia thereof.

Tissue characterisation is of fundamental interest in medical diagnosis, especially for estimating a rupture risk of an atheromatous plaque. For the last twenty years, a new medical imaging method has been developed. It is the ultrasonic elastography.

Based on the same principles as palpation, elastography locally studies the elastic behaviour of medium under the action of a stress. This study is based on the analysis of radiofrequency ultrasonic signals acquired before and after applying a stress, or acquired for different levels of stress.

As indicated above, the atherosclerosis plaque implies the deposit of lipids and/or collagen on the vessel walls. This deposit results in an increased or decreased elasticity of the vessel walls. The ultrasonic elastography provides the practitioner information enabling him/her to estimate the rupture risks of an atheromatous plaque.

EP 0 908 137 describes an ultrasonic elastography method enabling an image of the elastic characteristics of the medium to be provided. More precisely, this method enables a local apparent "stiffness" of the endoluminal thick layer of a cavity of a body such as an artery to be determined and displayed. However, this method has major drawbacks questioning the credibilities (i.e. they are not real elasticities) of the formulations of local and global elasticity respectively described in EP 0 908 137.

Especially, the local elasticity of the endoluminal thick layer of the cavity of the body is estimated assuming that:
the inner and outer walls of the body are cylindrical and concentric (i.e. uniform thickness of the body between the inner and outer cylindrical walls of the cavity),
both inner and outer walls of the body are subjected to uniform spatial pressure distributions,
such that the elasticity values supplied by implementing this method are very different from the real elasticity values of the analysed body and thus have no physical meaning (i.e. this is not a real elasticity).

Thus, the method described in EP 0 908 137 does not enable the practitioner to have sufficiently accurate available information to carry out a diagnosis. One purpose of the present invention is to provide an ultrasonic elastography method enabling the drawbacks of the method described in EP 0 908 137 to be overcome.

SUMMARY

To that purpose, the invention provides an imagine processing method which enables an elasticity image of a body including a cavity to be produced on the basis of the material(s) forming said body, characterised in that the method comprises the steps of:
receiving a deformation image illustrating a field of movement of the points of the body on the basis of a pressure difference in the body,
estimating a shape function of the body from the deformation image,
calculating an elasticity image of the body on the basis of the shape function, of the pressure difference and of the deformation image.

Estimating a shape function of the body and using this shape function in calculating the elasticity image enables the geometry of the body to be taken into account in calculating the elasticity image. It is thus possible to obtain a coherent elasticity image, even for bodies with a complex geometry.

Preferred, but non-limiting aspects of the method according to the invention are as follows:
the step of estimating the shape function comprises:
detecting the inside and outside contours of the body from the deformation image to obtain a contour image,
assigning a homogenous elasticity distribution in the contour image to obtain a work image,
determining the shape function from the work image;
the step of estimating the shape function comprises performing a finite element analysis;
the step of calculating an elasticity image consists in calculating an elasticity image projected on the inner wall of the body to obtain a projected elasticity image of the body;
the method further comprises a step of superimposing the projected elasticity image of the body on an image of the body acquired by using an ultrasonic device;
the method further comprises a step of receiving a palpography field corresponding to the selection by a user of an area of the body that the user wants to study, the step of calculating an elasticity image of the body being implemented on the palpography field;
the step of calculating an elasticity image comprises resolving the following equation:

$$E_{palpo}^{revisited}(\theta) = \frac{3}{2} \frac{\left| \int_{R_i(\theta)}^{R_p(\theta)} h*(r,\theta) dr \right|}{\left| \int_{R_i(\theta)}^{R_p(\theta)} \varepsilon_{rr}(r,\theta) dr \right|} \Delta P$$

with:
θ, the angular position in the body,
r, the radial position in the body,
ΔP the pressure difference,
$R_i(\theta)$ and $R_p(\theta)$ the inner and outer radii of a palpography field on the basis of the angular position in the body,
  h*(r,θ) the approximated shape function of the body on the basis of the radial and angular positions in the body,
  $\epsilon_{rr}(r,\theta)$ the real radial deformation of the body on the basis of the position in the body.

The invention also relates to a computer programme product including a program code recorded on a computer-readable data medium to execute the abovementioned method, when the computer programme is applied to a computer in order to be executed.

BRIEF DESCRIPTION OF THE FIGURES

Further features and advantages of the invention will appear from the following description, which is purely illustrative and non-limiting and must be read in comparison with the appended drawings, in which.

DETAILED DESCRIPTION

An exemplary method which can be applied to a body including a cavity and enabling information related to the body elasticity at the inner wall of its cavity to be supplied in real time will now be described more in detail. Hereinafter, the method will be described with reference to the study of blood vessels. However, it is obvious for those skilled in the art that this method can be applied to other types of bodies including a cavity, such as the heart or any industrial structures containing a cavity and where the deformation is quantified around this cavity.

In the case of an atheromatous plaque, the method generally comprises the steps of:
  receiving a deformation image illustrating a field of movement or of deformation of the points of the plaque,
  receiving a pressure difference in the plaque,
  estimating a shape function of the plaque by using the deformation image and the pressure difference,
  calculating an elasticity image of the plaque on the basis of the shape function, of the pressure difference, and of the deformation image.

These various steps will be described more in detail hereinafter.

Figure 1:
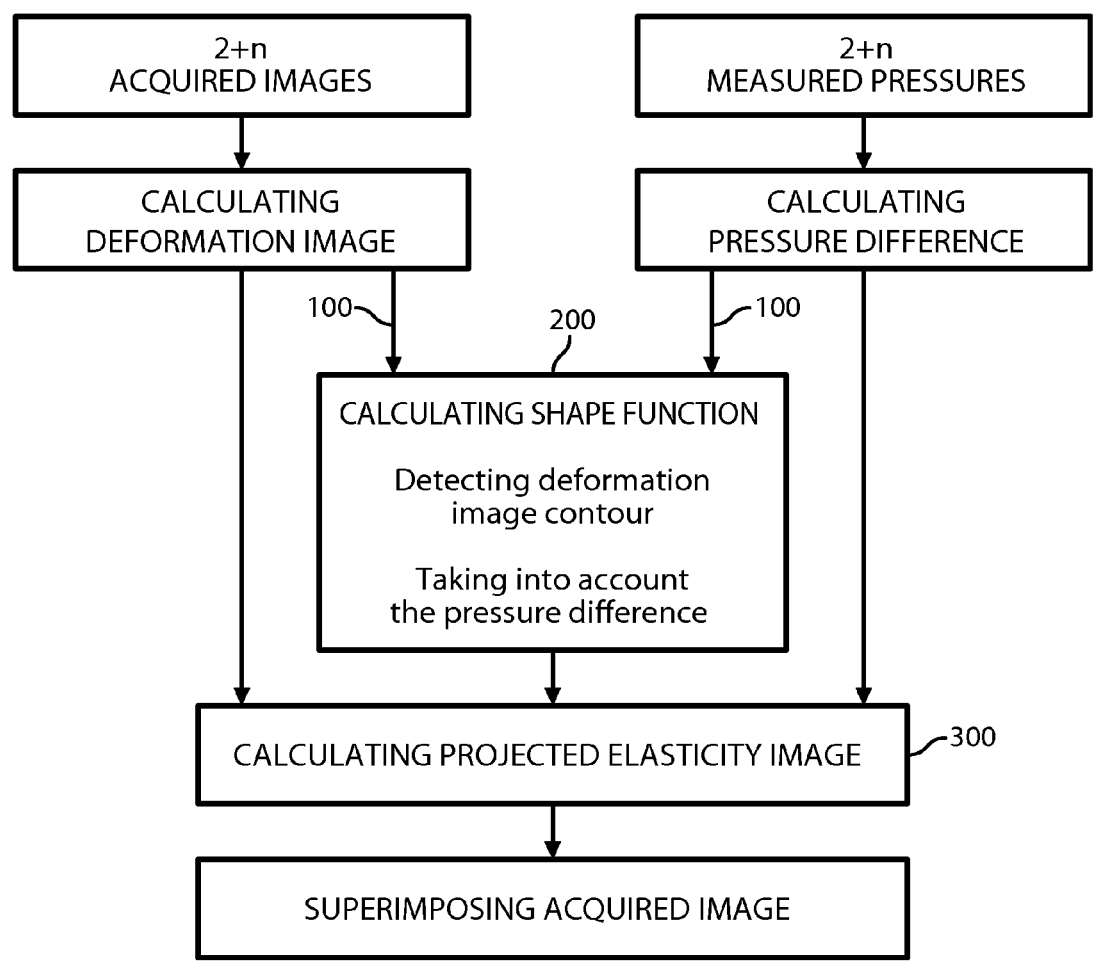
FIG. 1 illustrates the steps of the suggested method for calculating the elasticity of an atheromatous plaque.

1. Steps of the Method
1.1 Receiving a Mapping Image of Deformation/Movement of the Points Forming the Body Comprising a Cavity With reference to FIG. 1, the method comprises a step of receiving 100 a deformation image—referred to as an "elastogram"—illustrating a field of movement or deformation of the points of the body on the basis of a pressure difference in the body. The elastogram represents the inner deformations resulting from the compression of the analysed body—here a vascular blood tissue—on the basis of the blood pressure. The elastogram can be obtained by any method known by those skilled in the art.

For example, the elastogram can be obtained in the following way. An ultrasonic probe is introduced into an artery of a patient at an artery portion the analysis of which is desired. A sequence of ultrasonic images of the artery portion is acquired while the artery tissue is compressed/extended under the effect of the heartbeat. The elastogram is obtained by studying the kinetics of the time sequence of ultrasonic images.

Especially, the kinetic study can comprise the steps of:
  comparing two different images of the artery portion acquired at two distinct times of a heart cycle, said different images being acquired for two different stresses exerted on the artery portion,
  determining a map of movements by comparing the position of each of the points or pixels between both different images,
  determining a difference in the arterial pressure between both different images by subtracting the arterial pressures measured while acquiring said different images.

A deformation image—or elastogram—of the artery portion on the one hand, and the pressure difference which enabled this deformation image to be obtained on the other hand are obtained. Both pieces of information (i.e. mapping of the movements/deformations of the analysed body, and pressure difference associated with the mapping of the movements) are useful to implement a subsequent step of determining the elasticity of the inner wall of the body cavity.

1.2. Determining the Inside and Outside Contours of the Body

The method also comprises a step of detecting the inside and outside contours of the artery portion, and more precisely of the deformation image. Detecting the contours of the body including the cavity enables the quantity of data contained in the image to be significantly decreased and suppresses non-relevant information for implementing the method, while preserving the essential structural properties of the image.

The step of detecting the inside and outside contours of the image can be based on any technique known by those skilled in the art. It can be based for example on a search algorithm of extrema of an energy function calculated from characteristics of the images describing the object to be detected such as ridge, contour, or gradient information; texture attributes; distributions of grey shade levels or any other functions of grey shade levels or colours of the images; time information (optical flow, correlation or others); and a priori information regarding the aspect or the shape of the body to be detected. The step of detecting the contour enables a contour image of the body representing the inside contour (i.e. the lumen) of the artery portion, and the outside contour of the artery portion to be obtained.

1.3 Determining a Shape Function

The method also comprises a step of determining 200 a shape function of the artery portion. This step of determining the shape function is implemented:
  from the contour image obtained upon implementing the step of detecting a contour; and by supposing a homogeneous elasticity distribution between inner and outer walls of the contour image.

The step of determining an approximate shape function consists in finding a function "h*" describing at best the real shape (described by the function "h" the approximation of which is wanted) of the artery portion represented in the contour image. Preferably, the shape function "h*" is determined by using a method of finite elements known by those skilled in the art:

Given an unknown function h(M) the evaluation of which in any point M is wanted, the approximation will consist in finding a function h* best approximating h. The approximation h* is built in a base which is chosen, this approximation base is preferably polynomial in the case of finite elements. The number of terms of the base, noted as n, gives the number of points MI for which the approximation h* is equal to the function h:

$\forall I$ from 1 to $n, h^*(MI) = h(MI)$.

1.4. Determining the Elasticity Mapping

The method also comprises a step of estimating 300 the elasticity of the body, especially the elasticity of the body projected on the inside wall of the artery portion. This projected elasticity is estimated from:
the deformation image—or elastogram—of the body,
the luminal pressure difference ΔP between the images which enabled the deformation image to be obtained, and
the shape function h* estimated for the body.

Thus and unlike the method described in EP 0 908 137, the method according to the invention takes into account the shape of the cavity to supply an image of the elastic characteristics of the body. This enables an elasticity image the values of which are closer to the real elasticity values to be obtained. This also enables the detection risks of false negatives to be limited. Indeed, with the method described in EP 0 908 137, a large number of false negatives are detected, making the tool for detecting a rupture risk of an atheromatous plaque unusable for the user.

1.5. Operating Principle

The method according to the invention enables information regarding the elasticity of an atheromatous plaque to be supplied in real time. This information enables a user to predict a rupture risk of the plaque and to define whether it is necessary or not to perform a thorough study of the structure of this atheromatous plaque.

The operating principle is as follows. The user inserts an ultrasonic probe into the artery of a patient. For a given artery portion, the user selects a region of interest around the probe: this region of interest defines a palpography field (which can correspond to the whole section of the artery or be included in the latter). It is noted that this palpography field is the endoluminal thick layer of the body cavity and is noted as $\Omega_{palpo}$.

Ultrasonic images are acquired by using the probe. The blood pressure inside the artery is measured for each acquired image. From two of these images, a deformation image is calculated as well as a pressure difference corresponding to the difference between the blood pressures ΔP associated with both images.

A shape function is also estimated from one of the acquired images or the deformation image. The shape function h* is estimated by detecting the inside and outside contours of the plaque in the considered image, and by performing a finite element analysis. The deformation image, the pressure difference and the shape function are used to calculate an elasticity image projected on the inner side wall of the artery portion. This elasticity image is for example superimposed to an ultrasonic image acquired by using the probe, the different elasticity values being represented using a colour code in order to enable the user to quickly decide whether the studied artery portion is healthy, or whether the studied artery portion has a risk and requires implementing additional examinations. Certain theoretical aspects of the invention will be now described more in detail.

2. Theory Related to the Method According to the Invention

There are methods for in vivo characterising coronary atherosclerosis plaques (or atheromatous plaques) and for predicting their spontaneous rupture based on ultrasonic elastography. However, these methods do no enable a Young's modulus of the plaque to be determined in real time. Indeed, these methods use complex algorithms based on iterative and non-linear mathematical optimization tools in the field of continuum mechanics.

EP 0 908 137 describes a method for determining and displaying in real time a local apparent stiffness of the atheromatous plaque. However, this method does not take into account the complex geometry of the atheromatous plaque when determining a local apparent stiffness. Indeed, in the case of EP 0 908 137, it is assumed that:

the atheromatous plaque has a cylindrical shape, the atheromatous plaque is made of a homogeneous isotropic incompressible medium, and the atheromatous plaque is subjected to a uniform distribution of the outer radial stresses.

These hypotheses do not enable information about the mechanical properties of the plaque usable by the user to be obtained in order to estimate a rupture risk of the plaque.

The method according to the invention enables the drawbacks of the method described in EP 0 908 137 to be overcome thanks to the use of a shape function, by taking into account both:

the plaque geometry, and the palpography field geometry corresponding to an area of interest selected by a user, during the step of calculating the elasticity image of the plaque.

The defects of the method described in EP 0 908 137 have been resolved based on the inventors' reflection described below:

Based on the relationship (1) between the radial deviatoric stress $\sigma_{rr}^{dev}(r,\theta)$ the Young's modulus $E(r,\theta)$, and the radial deformation component $\epsilon_{rr}(r,\theta)$ for an elastic linear incompressible isotropic heterogeneous, and linear continuum:

$$\sigma_{rr}^{dev}(r,\theta) = \frac{2}{3}E(r,\theta)\varepsilon_{rr}(r,\theta) \quad (1)$$

Here $(r, \theta)$ is the system of polar coordinates referred to as the centre of gravity of the cavity inside which the blood flows.

The stress-deformation modulus $E_{palpo}^{new}(\theta)$ has been redefined as being equal to the ratio of the average deviatoric radial stress to the average radial deformation along a radial axis:

$$E_{palpo}^{new}(\theta) = \frac{3}{2} \frac{\left| \int_{R_i(\theta)}^{R_p(\theta)} \sigma_{rr}^{dev}(r,\theta) dr \right|}{\varepsilon(\theta)} \quad (2)$$

with $\varepsilon(\theta) = |\int_{R_i(\theta)}^{R_p(\theta)} \varepsilon_{rr}(r,\theta) dr|$, where $R_i(\theta)$ and $R_p(\theta)$ are the inner and outer radii of the palpography field.

Furthermore, knowing that the radial deformation $\varepsilon_{rr}(r,\theta)$ is proportional to the pressure difference $\Delta P$ (between the two images which enabled the deformation image to be obtained) and inversely proportional to the amplitude of the Young's modulus $E(r,\theta)$ there is:

$$\varepsilon_{rr}(r,\theta) = \frac{3}{2} \frac{\Delta P}{E(r,\theta)} h(r,\theta) \quad (3)$$

(where the constant 3/2 was introduced only for mathematical convenience).

The expression of the deviatoric radial stress of equation (1) can then be reformulated in the following way:

$$\sigma_{rr}^{dev}(r,\theta) = \Delta P h(r,\theta) \quad (4)$$

where $h(r,\theta)$ is a new corrective shape function taking into account the whole morphology of the plaque, including the geometrical heterogeneities of the plaque.

Taking into account this new expression of the deviatoric radial stress, the stress-deformation modulus $E_{palpo}^{new}(\theta)$ becomes:

$$E_{palpo}^{new}(\theta) = \frac{3}{2} \frac{\Delta P \left| \int_{R_i(\theta)}^{R_p(\theta)} h(r,\theta) dr \right|}{\varepsilon(\theta)} \quad (5)$$

Since the shape function $h(r,\theta)$ is unknown and cannot be directly measured, an approximate corrective shape function $h^*(r,\theta)$ is estimated.

This estimated shape function $h^*(r,\theta)$ is obtained by a finite element analysis technique, and by considering that the plaque is homogeneous, isotropic, and nearly incompressible with the Young's modulus E. The finite element analysis was implemented in a linear elastic medium for a blood pressure difference $\Delta P$. As a result, from equation (3) and knowing thanks to this finite element calculation the distribution of radial deformations in space $\varepsilon_{rr}^{iso}(r,\theta)$ the estimated shape function $h^*(r,\theta)$ is extracted:

$$h^*(r,\theta) = \frac{2}{3} \frac{E}{\Delta P} \varepsilon_{rr}^{iso}(r,\theta) \quad (6)$$

which is used to improve the formula of the stress-deformation modulus and becomes:

$$E_{palpo}^{revisited}(\theta) = \frac{3}{2} \frac{\Delta P \left| \int_{R_i(\theta)}^{R_p(\theta)} h^*(r,\theta) dr \right|}{\varepsilon(\theta)} \quad (7)$$

This original formula of the stress-deformation modulus (Equation 7) enables the Young's modulus of amplitude E to be obtained again by considering the plaque to be isotropic and homogeneous (i.e. $E_{palpo}^{revisited}(\theta) = E$), whatever the geometry of the plaque and the considered palpography field $\Omega_{palpo}$ (with $R_i(\theta) \leq r \leq R_p(\theta)$).

3. Comparison of Results Obtained with the Method According to the Invention Relative to the Results Obtained with the Method Described in EP 0 908 137

Figure 2:
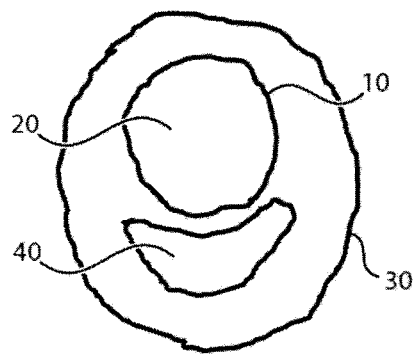
FIG. 2 illustrates the atheromatous plaque.

FIG. 2 illustrates an exemplary plaque on which the method described in EP 0 908 137 and the method according to the invention have been implemented to allow a comparison of the obtained results. The plaque is a cross-section artery portion. It comprises an inside wall 10 defining a cavity 20 inside which the blood flows, and an outside wall 30 defining the outer surface of the artery. The plaque also comprises a space 40 filled with a segmental accumulation of lipids.

Figure 3:
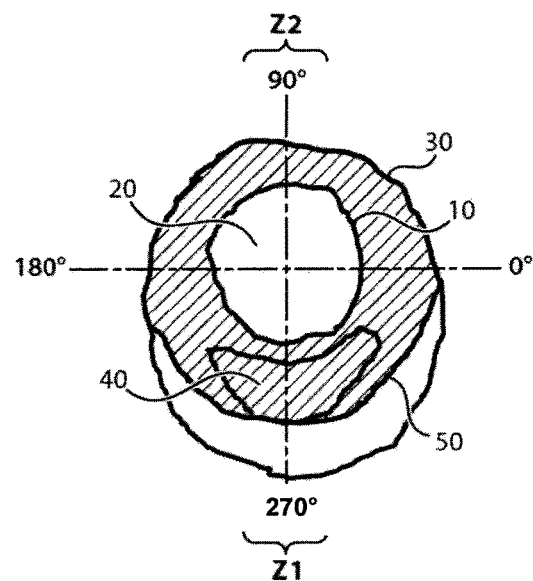
FIG. 3 illustrates the endoluminal thick layer of the body cavity.

FIG. 3 illustrates this same plaque on which the palpography field $\Omega_{palpo}$ limited by the inside wall 10 and the considered intra-parietal wall 50 has been illustrated. It is noted that in this example the space 40 is included in the palpography field. An orthonormal benchmark is also represented to enable angular positions on the plaque to be matched with the angular positions indicated in the graph of FIG. 4.

Figure 4:
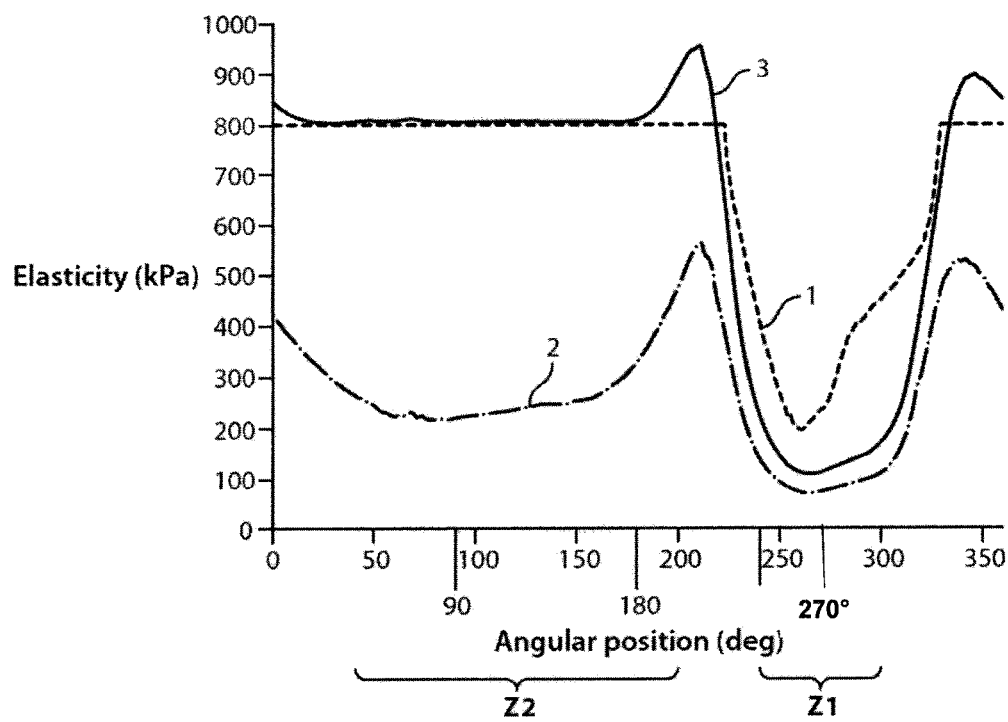
FIG. 4 illustrates a graph of the calculated elasticities of a plaque on the basis of the angular position on the plaque and shows that the real elasticity can be obtained thanks to our approach.

FIG. 4 is a graph representing an elasticity on the basis of the angular spatial position ($0° \leq \theta \leq 360°$). Three curves are illustrated:
- a first curve 1 corresponds to the real elasticity of the plaque,
- a second curve 2 corresponds to the elasticity of the plaque calculated by using a method described in EP 0 908 137,
- a third curve 3 illustrates the elasticity of the plaque calculated by implementing the method according to the invention.

As can be noticed, the calculated elasticity values represented on the second curve are very different from the real elasticity values represented on the first curve.

Moreover, by using the method described in EP 0 908 137, two soft areas are detected, as represented on the second curve:
- a first soft area Z1 corresponds to the lower part of the artery in which the space 40 is located;
- a second soft area Z2 corresponds to the upper part of the artery.

Thus, the method described in EP 0 908 137 seems to indicate two potentially at risk areas to the user, whereas the upper area has no risk and simply corresponds to a thinner area of the artery. This is due to the fact that the hypotheses used in the method of EP 0 908 137 (i.e. cylindrical and concentric inner and outer walls of the plaque) do not enable:
- a soft area in the artery,
- a thin artery in the artery,
to be distinguished.

Thus, the method of EP 0 908 137 induces the detection of a large number of false negatives tending to make information supplied to a user unusable. On the contrary, as illustrated on the third curve, the elasticities calculated with the method according to the invention are close to the real elasticities of the plaque. Furthermore, no false negative is detected: only the first soft area Z1 induces a variation in the elasticity. The above described method thus enables real time information usable by the user to be supplied, enabling him/her to predict the rupture risks of an atheromatous plaque.

The invention claimed is:

1. An imaging processing method which produces an elasticity image of a body including a cavity depending on material(s) forming the body, wherein the method comprises:
   receiving a deformation image and a cavity image of the cavity from an ultrasonic probe, the deformation image illustrating a field of movement of points of the body depending on a pressure difference in the body;
   estimating a shape function of the body from the deformation image;
   calculating an elasticity image of the body depending on the shape function, on the pressure difference, and on the deformation image;
   superimposing the elasticity image on the cavity image; and
   displaying the superimposed elasticity image,
   wherein the step of calculating the elasticity image comprises resolving the following equation:

$$E_{palpo}^{revisited}(\theta) = \frac{3}{2} \frac{\left|\int_{R_i(\theta)}^{R_p(\theta)} h*(r,\theta)dr\right|}{\left|\int_{R_i(\theta)}^{R_p(\theta)} \varepsilon_{rr}(r,\theta)dr\right|} \Delta P$$

with:
   $E_{palpo}^{revisited}(\theta)$, a stress-deformation modulus depending on the angular position in the body,
   $\theta$, an angular position in the body in a system of polar coordinates originating at a center of gravity of the cavity,
   r, the radial position in the body in the system of polar coordinates,
   $\Delta P$, the pressure difference,
   $R_i(\theta)$ and $R_p(\theta)$, inner and outer radii of a palpography field depending on the angular position in the body,
   $h*(r,\theta)$, the estimated shape function of the body depending on the radial and angular positions in the body, and
   $\varepsilon_{rr}(r,\theta)$, a real radial deformation of the body depending on the radial and angular positions in the body.

2. The method according to claim 1, wherein the step of estimating the shape function comprises:
   detecting inside and outside contours of the material(s) forming a wall of the cavity from the deformation image to obtain a contour image;
   assigning a homogeneous distribution of elasticity in the contour image to obtain a work image; and
   determining the shape function from the work image.

3. The method according to claim 1, wherein the step of estimating the shape function comprises implementing a finite element analysis.

4. The method according to claim 1, wherein the step of calculating the elasticity image comprises calculating an elasticity image projected on an inner wall of the body to obtain a projected elasticity image of the body.

5. The method according to claim 1, further comprising a step of receiving a palpography field corresponding to a selection by a user of an area of the body that the user wants to study, the step of calculating the elasticity image of the body being implemented on the palpography field.

6. A non-transitory computer program product which produces an elasticity image of a body including a cavity depending on material(s) forming the body, comprising a program code recorded on a computer-readable data medium, the program code, when executed by a processor, causes the steps of:
   receiving a deformation image and a cavity image of the cavity from an ultrasound probe, the deformation image illustrating a field of movement of points of a body depending on a pressure difference in the body;
   estimating a shape function of the body from the deformation image;
   calculating an elasticity image of the body depending on the shape function, on the pressure difference, and on the deformation image; and
   causing a display to superimpose the elasticity image on the cavity image,
   wherein the program code calculating the elasticity image uses the following equation:

$$E_{palpo}^{revisited}(\theta) = \frac{3}{2} \frac{\left|\int_{R_i(\theta)}^{R_p(\theta)} h*(r,\theta)dr\right|}{\left|\int_{R_i(\theta)}^{R_p(\theta)} \varepsilon_{rr}(r,\theta)dr\right|} \Delta P$$

with:
   $E_{palpo}^{revisited}(\theta)$, a stress-deformation modulus depending on the angular position in the body,
   $\theta$, an angular position in the body in a system of polar coordinates originating at a center of gravity of a cavity,
   r, the radial position in the body in the system of polar coordinates,
   $\Delta P$, the pressure difference,
   $R_i(\theta)$ and $R_p(\theta)$, inner and outer radii of a palpography field depending on the angular position in the body,
   $h*(r,\theta)$, the estimated shape function of the body depending on the radial and angular positions in the body, and
   $\varepsilon_{rr}(r,\theta)$, a real radial deformation of the body depending on the radial and angular positions in the body.

7. The computer program product of claim 6, wherein the program code receives the deformation image from an ultrasonic probe.

8. The computer program product of claim 6, wherein the elasticity image is implemented on a palpography field.

* * * * *